(12) United States Patent
Ciechanowski et al.

(10) Patent No.: US 7,682,562 B2
(45) Date of Patent: Mar. 23, 2010

(54) OZONE-GENERATING METHOD FOR TUBS

(75) Inventors: Dominique Ciechanowski, Sainte-Marguerite de Dorchester (CA); Miguel Castellote, Sainte-Marguerite de Dorchester (CA)

(73) Assignee: C.G. Air Systèmes Inc., Sainte-Marguerite-De-Dorchester, Québec (CA)

( * ) Notice: Subject to any disclaimer, the term of this patent is extended or adjusted under 35 U.S.C. 154(b) by 0 days.

(21) Appl. No.: 11/947,133

(22) Filed: Nov. 29, 2007

(65) Prior Publication Data
US 2008/0131314 A1 Jun. 5, 2008

Related U.S. Application Data

(60) Provisional application No. 60/867,640, filed on Nov. 29, 2006.

(51) Int. Cl.
*A61L 2/20* (2006.01)
(52) U.S. Cl. ............... 422/28; 422/186.07; 4/541.1; 4/541.4
(58) Field of Classification Search ............ 422/186.07, 422/28; 4/541.1, 541.4
See application file for complete search history.

(56) References Cited

U.S. PATENT DOCUMENTS

| 6,317,903 | B1 * | 11/2001 | Brunelle et al. | ............. 4/541.4 |
| 6,405,387 | B1 * | 6/2002 | Barnes | ............. 4/541.2 |
| 6,723,233 | B1 * | 4/2004 | Barnes | ............. 210/167.11 |
| 2006/0053546 | A1 * | 3/2006 | Gloodt | ............. 4/541.1 |

FOREIGN PATENT DOCUMENTS

JP         53011897 A  *  2/1978

OTHER PUBLICATIONS

Derwent English abstract for JP 53011897A, Inventor: Kawachi et al., Published: Feb. 1978.*
"in.zone" ozone generator, as found on Internet website http://www.geckoalliance.com/aeware/produit_features.php?nom=zone.

* cited by examiner

*Primary Examiner*—Sean E Conley
(74) *Attorney, Agent, or Firm*—Ogilvy Renault

(57) ABSTRACT

A system for decontaminating a fluid-injection system for a tub from organic growth comprises an ozone source and a pressure source, producing an ozone-enriched air output. Piping is connected to a fluid-injection system. A controller device actuates the ozone source and the pressure source such that the ozone-enriched air output is conveyed to conduits of the fluid-injection system. A switch manually actuated to stop an actuation of the ozone source, whereby organic growth in the conduits of the fluid-injection system is exposed to the ozone-enriched air output.

5 Claims, 3 Drawing Sheets

OZONE-GENERATING METHOD FOR TUBS

CROSS-REFERENCE TO RELATED APPLICATION

This patent application claims priority on U.S. Provisional Application No. 60/867,640, filed on Nov. 29, 2006.

BACKGROUND OF THE APPLICATION

1. Field of the Application

The present application generally relates to tubs and, more particularly, to the decontamination of fluid-injection systems for tubs that inject fluid into a tub so as to create a massaging-effect turbulence in the liquid of the tub.

2. Background Art

Tubs are well known for their primary use, namely a washroom installation in which a user person washes and/or bathes. Tubs have, however, evolved to add relaxation and comfort to practicality, and are found in many forms, such as bathtubs, spas, whirlpools.

For instance, tubs are now provided with air-jet systems or hydro-massage systems. Such systems often involve piping to inject a fluid (air, water) into the water of the tub, so as to cause a turbulence that will create a massaging effect on the occupant of the tub.

The piping is connected to openings in the wall of the tub for fluid injection therethrough. Even though various mechanisms have been provided to prevent infiltration (e.g., check valves at the jets), water has been known to infiltrate the piping through these openings, to accumulate in the piping. Water accumulated therein is stagnant, and is subject to mildew, alga and/or bacteria growth.

In order to decontaminate the piping, it is known to inject ozone so as to oxidize organic growth and kill same. However, ozone is noxious at low concentrations, whereby the use of ozone in piping decontamination must be highly controlled in residential installations.

SUMMARY OF APPLICATION

It is an aim of the present application to provide a system for decontaminating piping of fluid-injection systems for tubs which overcomes disadvantages of the prior art.

It is a further aim of the present application to provide a method for decontaminating piping of fluid-injection systems for tubs which overcomes the disadvantages of the prior art.

Therefore, in accordance with the present application, there is provided a method for decontaminating a fluid-injection system of a tub from organic growth, comprising: providing an ozone-enriched air source in connection with the fluid-injection system; determining when the ozone-enriched air source is to be actuated; automatically creating a flow of ozone-enriched air from the ozone-enriched air source within conduits of the fluid-injection system; and automatically circulating ozone-free air within the conduits of the fluid-injection system to remove ozone from the conduits.

Further in accordance with the present application, there is provided a system for decontaminating a fluid-injection system for a tub from organic growth, comprising: an ozone source and a pressure source, producing an ozone-enriched air output; piping adapted to be connected to a fluid-injection system; a controller device for actuating the ozone source and the pressure source such that the ozone-enriched air output is conveyed to conduits of the fluid-injection system; a switch manually actuatable to stop an actuation of the ozone source; whereby organic growth in the conduits of the fluid-injection system is exposed to the ozone-enriched air output.

DESCRIPTION OF THE PREFERRED EMBODIMENTS

Figure 1:
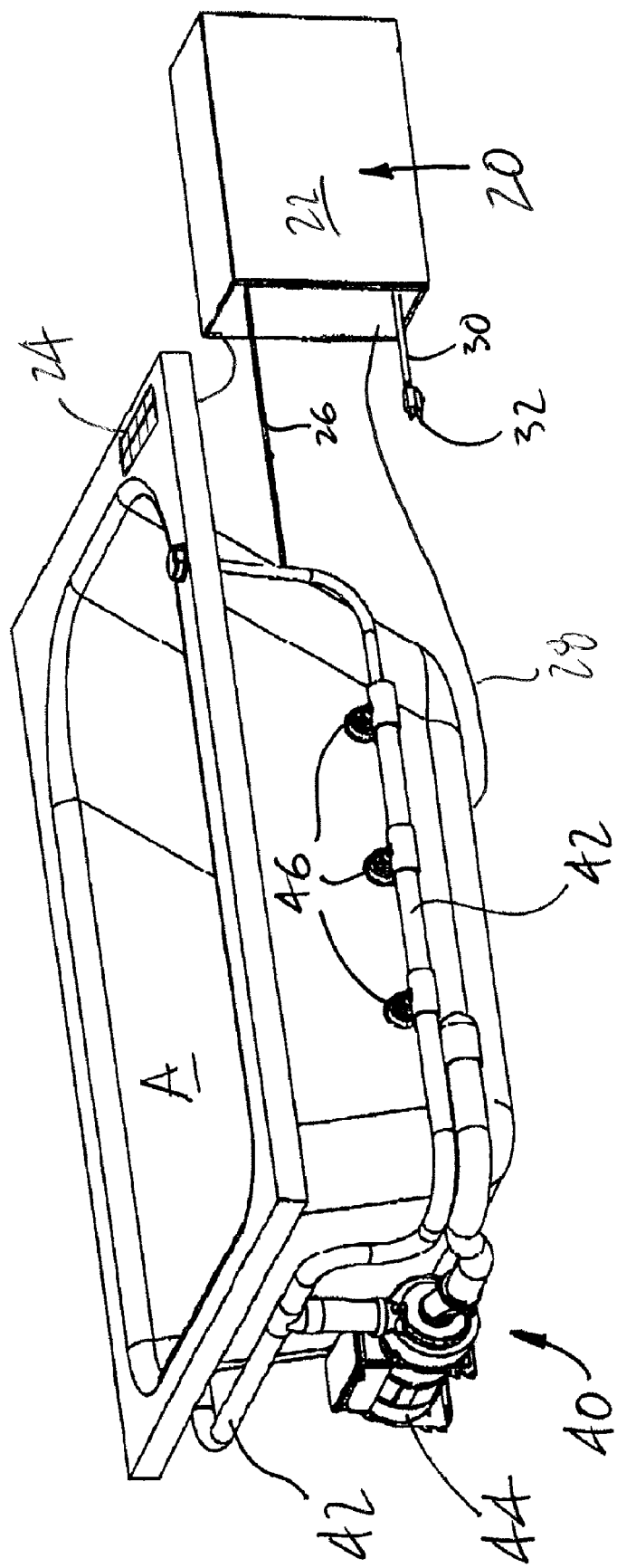
FIG. 1 is a perspective view of an ozone-generating system in accordance with an embodiment of the present application being used in conjunction with a hydro-massage system for a tub.

Referring to the drawings, and more particularly to FIG. 1, an ozone-generating system in accordance with an embodiment is generally shown at 20, and is provided to purify the conduits of fluid massaging systems. The ozone-generating system 20 takes the shape of a casing 22 in which an ozone generator is accommodated. The ozone generator produces ozone.

A pressure source is also enclosed in the casing 22, and is associated with the ozone generator such that the ozone output of the ozone generator is conveyed out of the system 20 by the flow of air produced by the pressure source. The ozone generator is any suitable system generating ozone for tubs and spas. For instance, it is considered to use a system generating ozone using corona discharge, or hybrid system combining corona discharge and UV lamps.

A controller device (e.g., a programmable processor) electronically controls the actuation of both the ozone generator and of the pressure source independently from one another. Accordingly, the controller device can maintain the pressure source "on" while the ozone generator is "off". The controller device is also within the casing 22, but has an optional interface 24 (e.g., a keyboard) that is positioned on a wall of the tub, for the user of the tub to stop the ozone-generating system 20, or view whether the ozone-generating system 20 is operational (e.g., via a LED). It is pointed out that the interface 24 may be part of the fluid-injection system (e.g., hydro-massage system 40 of FIG. 1 or air-injection system 50 of FIG. 2), with the controller device of the ozone-generating system 20 monitoring the systems 40/50 to actuate the ozone generator and pressure source. The interface 24 is optional in the ozone-generating system 20.

Piping 26 is provided in fluid communication with the ozone generator and pressure source of the ozone-generating system 20. The piping 26 extends out of the casing 22 to tap into a fluid-injection system, as will be illustrated hereinafter. A check valve (not shown) is typically provided with the piping 26 to ensure that liquid from the tub does not reach the ozone-generating system 20. Moreover, it is considered to provide Hartford loops in the piping 26 for safety purposes. In one embodiment (not shown), the piping 26 is wrapped about the casing 22 in Hartford loops.

A liquid level sensor 28 is connected to the controller device of the ozone-generating system 20. The liquid level sensor 28 is used to determine whether there is liquid in the tub, and is hence positioned around the bottom of the tub, in the conduits 42/52 or in other parts of the fluid-injection systems.

Wires 30 connect a power source to the electrically powered members of the ozone-generating system 20, such as the controller device, the ozone generator and the pressure source. A standard outlet plug 32 is provided at an end of one of the wires 30, at the exterior of the casing 22, for power supply.

Still referring to FIG. 1, the ozone-generating system 20 is shown as being used in conjunction with a hydro-massage system 40 (i.e., water-injection system). The hydro-massage system 40 is mounted to a tub A, and has conduits 42 by which water, collected in the tub A and pressurized by pump 44, is reinjected into the tub A through jets 46. The ozone generator system 20 taps into the conduits 42 by the piping 26. Therefore, the ozone-enriched air of the ozone generator system 20 is exhausted into the conduits 42. The ozone-enriched air will circulate in the conduits 42, and kill organic growth in the conduits 42.

Figure 2:
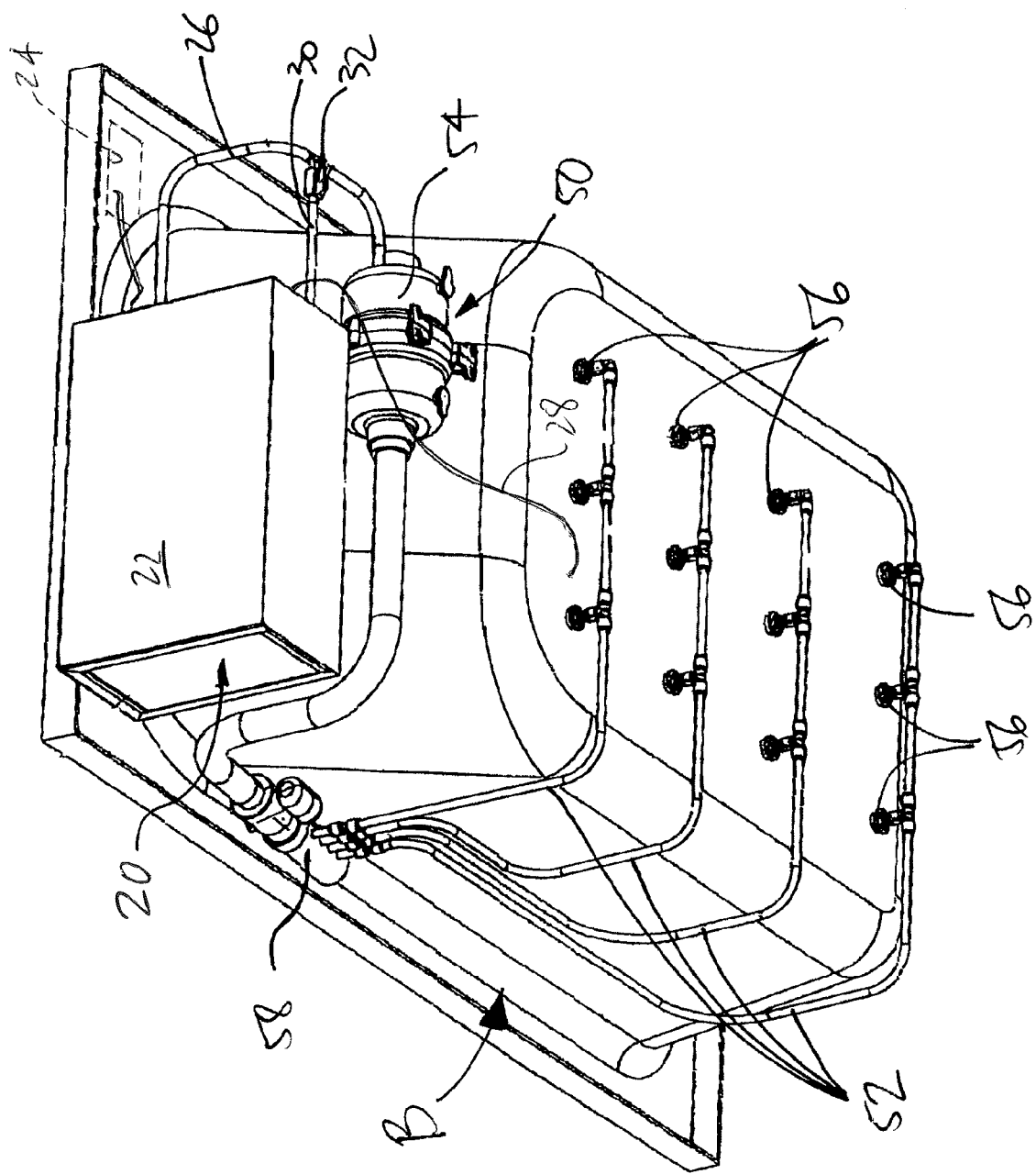
FIG. 2 is a perspective view of the ozone-generating system of FIG. 1 being used in conjunction with an air-injection system for a tub.

Referring to FIG. 2, the ozone-generating system 20 is shown being used with an air-injection system 50. The air-injection system 50 is mounted to a tub B, and has conduits 52 by which air, pressurized by blower 54, is injected into the tub water through jets 56 to create turbulence, hence providing a massaging effect on the user of the tub B. The ozone-generating system 20 is as illustrated in FIG. 1, and taps into the blower 54, such that ozone-enriched air of the ozone-generating system 20 is exhausted to the blower 54, which will direct the ozone-enriched air through the conduits 52, to kill organic growth therein (e.g., downstream of manifold 58). Ultimately, the ozone-enriched air will reach the tub B. In FIG. 2, the piping 26 is shown being connected to the air blower 54, but may also be connected to other parts of the fluid-injection system, such as the conduits 52.

Figure 3:
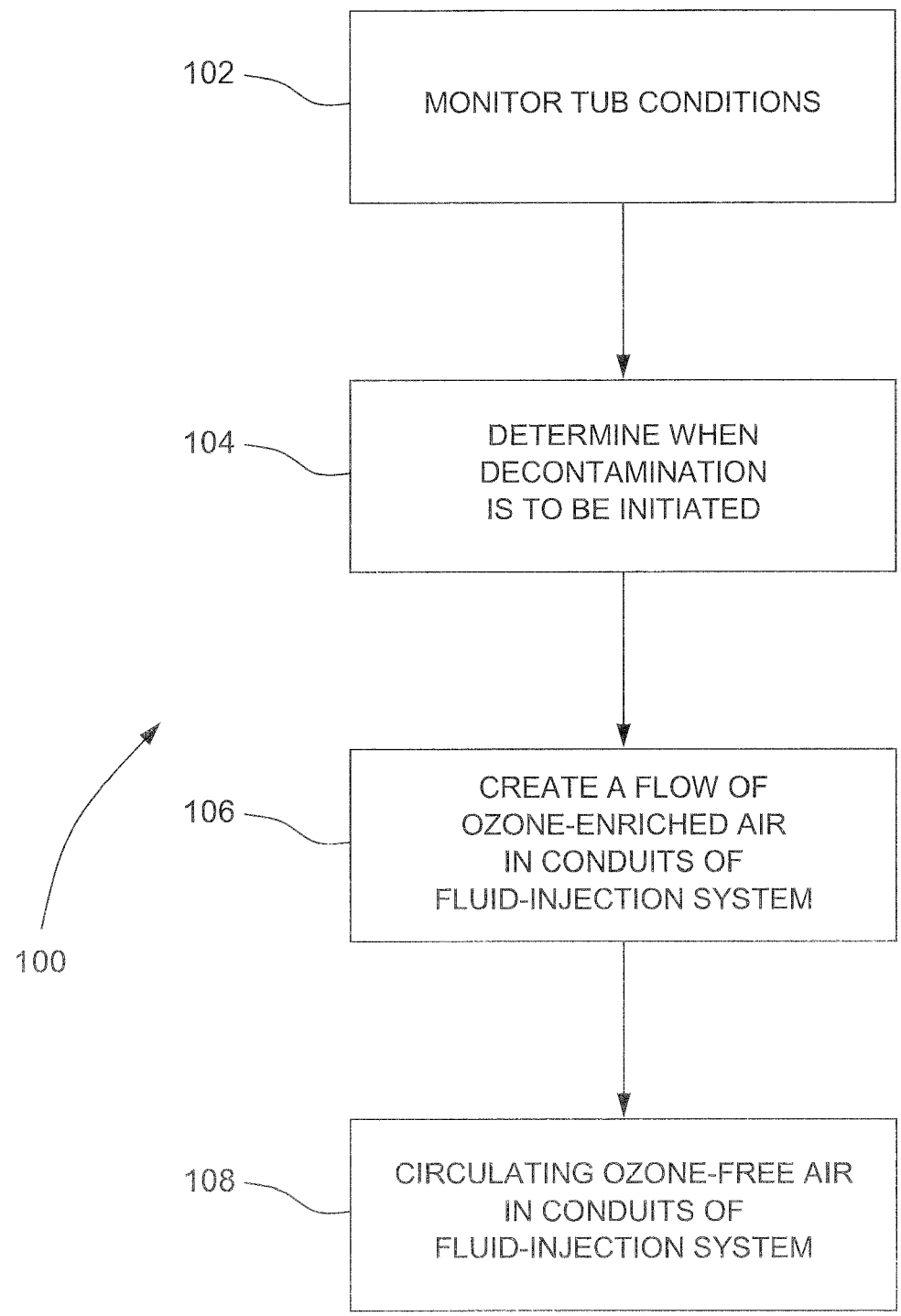
FIG. 3 is a flowchart illustrating a method for decontaminating a fluid-injection system using ozone generation, in accordance with another embodiment of the present application.

Now that the ozone-generating system 20 has been described, a contemplated sequence of operation thereof is described. The sequence of operation is illustrated in FIG. 3, in which a method 100 for decontaminating a fluid-injection system is described.

Referring to Step 102, the ozone-generating system 20 monitors the tub or the fluid-injection system (40/50) to assess the tub conditions. In the illustrated embodiment, the liquid level sensor 28 detects the presence of liquid in the tub. Alternative types of detectors may be used as well.

The tub conditions are monitored in order to determine when decontamination is to be initiated. Referring to Step 104, the controller device determines when decontamination is to be initiated.

The conditions by which the decontamination is to be initiated are set by the manufacturer, or by the user.

According to one embodiment, the ozone-generating system is in standby until the liquid level sensor 28 signals that the liquid has been emptied from the tub. The signaling of the empty tub will trigger a timer in the controller device for a preset amount of time at which ozone will be generated to purify the fluid lines. In an embodiment, the preset amount of time is 60 minutes.

According to Step 106, a flow of ozone-enriched air is created in the conduits of the fluid-injection system. More specifically, after the preset amount of time has lapsed, if the tub is still empty, the ozone generator and the pressure source of the ozone-generating system 20 will be actuated by the controller device to supply ozone to the fluid lines of the fluid massage systems 40/50. The ozone generator and the pressure source are actuated for a preset period, which preset period of time takes into consideration the fact that high concentrations of ozone can be hazardous to health. All safety measures must therefore be taken when using ozone to purify fluid lines.

According to Step 108, generally ozone-free air is circulated in conduits of the fluid-injection system. More specifically, once the preset period is finished, a specific step is performed to remove residual ozone from the liquid lines. The ozone generator is turned off while the pressure source is still operated. Accordingly, a flow of air without ozone is circulated through the fluid lines. This ensures that the various electronic components of the fluid massage systems 40/50 and of the ozone-generating system 20 will not be corroded by ozone. The delay between the end of actuation of the ozone generator and the pressure source is typically 15-20 seconds.

In the described embodiment, the ozone-generating system 20 is therefore fully automatic but may be manually turned off by the user. The ozone-generating system 20 may be retrofitted to existing fluid massage systems, and may use the keypad of an existing fluid massage system.

It is within the ambit of the present application to cover any obvious modifications of the embodiments described herein, provided such modifications fall within the scope of the appended claims.

The invention claimed is:

1. A method for decontaminating a fluid-injection system of a tub from organic growth, comprising:
   providing an ozone-enriched air source in connection with the fluid-injection system;
   determining when the ozone-enriched air source is to be actuated by monitoring the fluid-injection system and/or tub for the absence of a liquid;
   initiating a timer for a preset amount of time after the absence of the liquid is detected;
   automatically creating a flow of ozone-enriched air from the ozone-enriched air source within conduits of the fluid-injection system after an end of the preset amount of time; and
   automatically circulating ozone-free air within the conduits of the fluid-injection system to remove ozone from the conduits.

2. The method according to claim 1, further comprising stopping any one of the creation of the flow of ozone-enriched air and the circulation of ozone-free air in response to a manual actuation of a user.

3. The method according to claim 1, wherein automatically creating a flow of ozone-enriched air is performed during a preset amount of time.

4. The method according to claim 1, wherein automatically creating a flow of ozone-enriched air is performed during a preset amount of time subsequent to automatically creating the flow of ozone-enriched air.

5. The method according to claim 1, wherein initiating a preset amount of time after the absence of the liquid is detected comprises setting the preset amount of time to 60 minutes.

* * * * *